United States Patent [19]

Moulton et al.

[11] Patent Number: 5,084,239

[45] Date of Patent: Jan. 28, 1992

[54] PLASMA STERILIZING PROCESS WITH PULSED ANTIMICROBIAL AGENT TREATMENT

[75] Inventors: Kern A. Moulton, Livermore; Bryant A. Campbell, Los Gatos, both of Calif.; Ross A. Caputo, Long Grove, Ill.

[73] Assignee: Abtox, Inc., Pleasanton, Calif.

[21] Appl. No.: 576,235

[22] Filed: Aug. 31, 1990

[51] Int. Cl.$^5$ .......................... A61L 2/14; A61L 2/20
[52] U.S. Cl. ...................................... 422/22; 422/23; 422/28; 250/455.1
[58] Field of Search ............................ 422/23, 28, 22; 250/455.1

[56] References Cited

U.S. PATENT DOCUMENTS 4,643,876 2/1987 Jacobs et al. .................. 422/28
4,756,882 7/1988 Jacobs et al. .................. 422/23

FOREIGN PATENT DOCUMENTS 0109352 5/1983 European Pat. Off. .
2214081 8/1989 United Kingdom .

OTHER PUBLICATIONS

Leaper article entitled "Influence of Temperature on the Synergistic Sporicidal . . . ", Food Microbiol., 1:199-203, 1984.

Leaper et al., article entitled "A Note on the Effect of Storage on The Chemical . . . ", J. Appl. Biol., 64:183-186, 1988.

Leaper article entitled "Synergistic Killing of Spores . . . ", J. Food Biol., 19:355-360, 1984.

Leaper article entitled "Comparison of the Resistance to . . . ", J. Food Technol., 19:695-702, 1984.

Primary Examiner—Jill Johnston
Assistant Examiner—Lyle A. Alexander
Attorney, Agent, or Firm—Majestic, Parsons, Siebert & Hsue

[57] ABSTRACT

A process for plasma sterilization comprising exposing an article in a sterilizing chamber to at least one cycle comprising a pulsed treatment with gaseous antimicrobial agent and a plasma treatment. The pulsed treatment comprises at least two pulse-vacuum cycles, each pulse-vacuum cycle comprising the steps of exposing the article to the gaseous antimicrobial agent at a pressure of from 4 to 18 torr and reducing the pressure in the sterilizing chamber to from 0.1 to 4 torr. The plasma treatment comprising exposing the article to a plasma generated from gases selected from the group consisting essentially of argon, helium, nitrogen, oxygen, hydrogen and mixtures thereof, the exposure to the plasma being carried out at a pressure of from 0.1 to 10 torr and a temperature of less than 80° C. The antimicrobial agent is selected from the group consisting of hydrogen peroxide, a peracid antimicrobial agent, and mixtures thereof, the peracid antimicrobial agent being selected from the group consisting of saturated and unsaturated peralkanoic acids having from 1 to 8 carbon atoms and halogenated derivatives thereof.

12 Claims, 3 Drawing Sheets

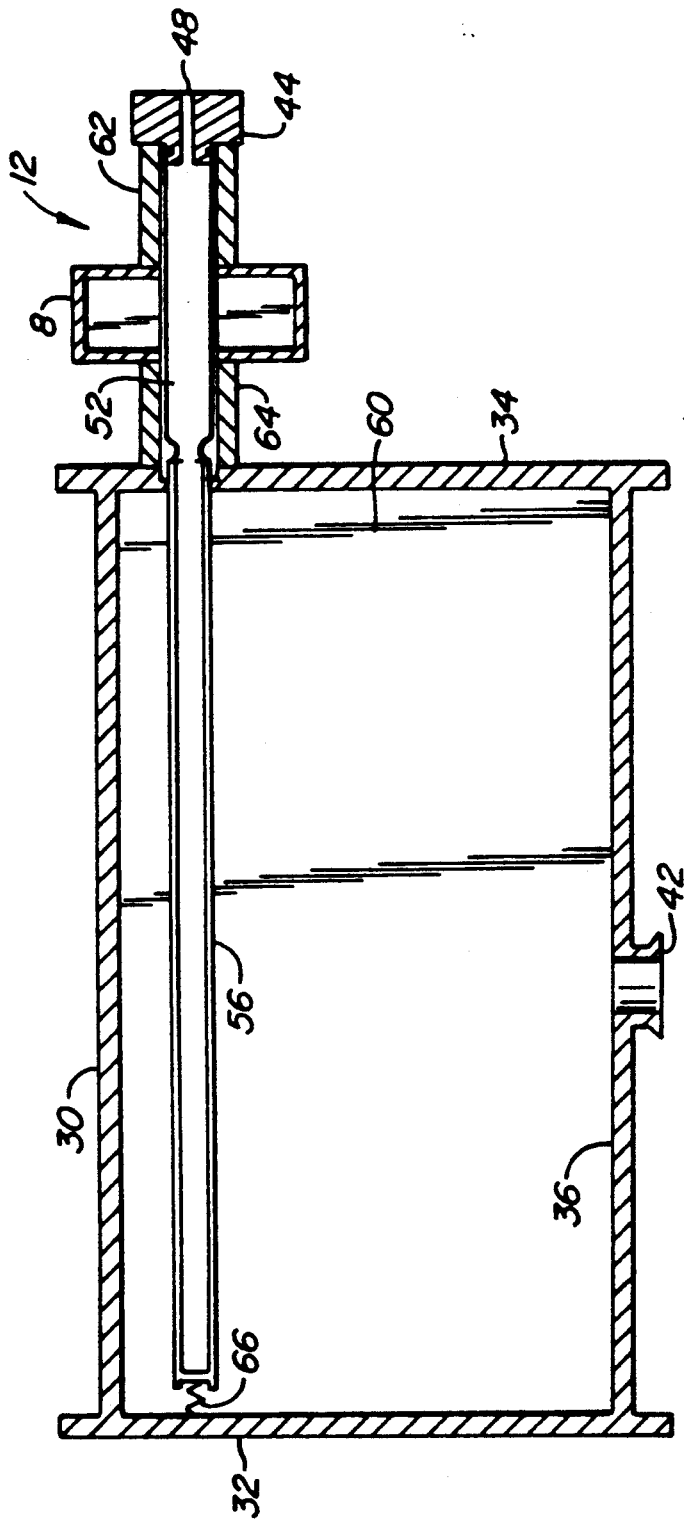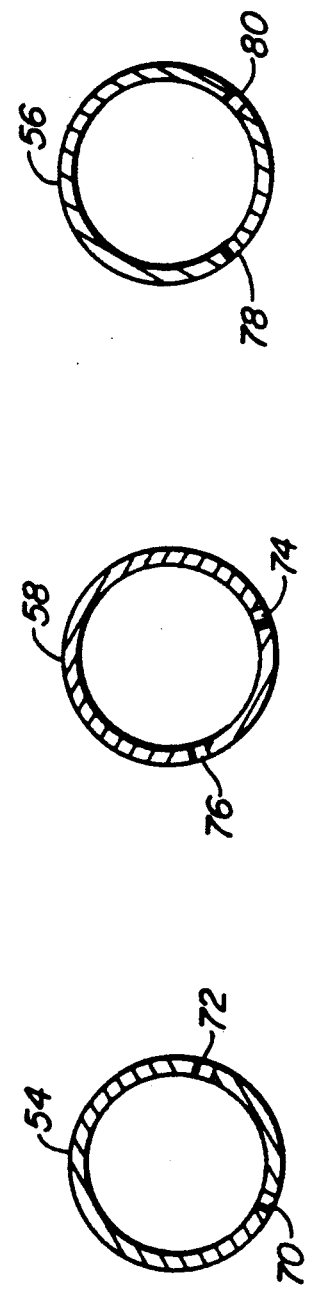

PLASMA STERILIZING PROCESS WITH PULSED ANTIMICROBIAL AGENT TREATMENT

COPENDING APPLICATIONS

The entire contents or one following commonly assigned, copending applications relating to the subject matter of this invention are hereby incorporated by reference:
  application Ser. No. 07/475,602 filed Feb. 6, 1990 by Bryant A. Campbell and Kern A. Moulton entitled PLASMA STERILIZER AND METHOD.
  application Ser. No. 07/522,271 filed May 11, 1990 by Bryant A. Campbell, Kern A. Moulton, and Ross A. Caputo entitled STERILIZING WITH PERACID AND PLASMA.
  application Ser. No. 07/522,421 filed May 11, 1990 by Bryant A. Campbell, Kern A. Moulton, and Ross A. Caputo entitled STERILIZING WITH HYDROGEN PEROXIDE AND PLASMA.
  application Ser. No. 07/576,294, filed Aug. 31, 1990 by K. A. Moulton, R. A. Caputo and B. A. Campbell entitled PLASMA CYCLING STERILIZING PROCESS.
  application Ser. No. 07/589,511 filed Sept. 28, 1990 by Bryant A. Campbell entitled CIRCULAR WAVEGUIDE PLASMA MICROWAVE STERILIZER APPARATUS.
  application Ser. No. 07/576,325 filed August 31, 1990 by K. A. Moulton, R. A. Caputo and B. A. Campbell entitled FLASH STERILIZATION WITH PLASMA.

FIELD OF THE INVENTION

This invention relates to a plasma sterilization process comprising pulsed treatment with a gaseous or vaporized antimicrobial agent such as hydrogen peroxide or a peracid to kill microorganisms and spores on the article. In particular, this invention relates to exposing an article to be sterilized to a plurality of treatment cycles, each cycle including cyclic pulses of a gaseous or vaporized antimicrobial agent at one pressure, followed by pressure reduction to a lower pressure. The article is then exposed to a gas plasma.

BACKGROUND OF THE INVENTION

A Variety of gas sterilization methods has been investigated in the past. Methods using ethylene oxide and other disinfecting gases are used for sterilizing a wide range of medical products from pharmaceutical preparations to surgical instruments. Irradiation alone or together with disinfecting gases has also been investigated, as summarized by Russell, A. THE DESTRUCTION OF BACTERIAL SPORES. New York: Academic Press (1982).

A sterilizing method must effectively kill all organisms, including spores, without damage to the article or goods being sterilized. However, many disinfecting gases which meet these criteria, such as ethylene oxide, and irradiation methods have been recognized to expose workers and the environment to safety hazards. States and Federal legislation are severely restricting the amount of hazardous gases such as ethylene oxide (a carcinogen) in the working environment, or the use of any system or method which produces toxic residues or exhaust products. This is presenting a major crisis in hospitals and other areas of the health industry.

DESCRIPTION OF THE PRIOR ART

Sterilizing plasmas have been generated with a wide variety of gases: argon, helium or xenon (U.S. Pat. No. 3,851,436); argon, nitrogen, oxygen, helium or xenon (U.S. Pat. No. 3,948,601); glutaraldehyde (U.S. Pat. No. 4,207,286); oxygen (U.S. Pat. No. 4,321,232); oxygen, nitrogen, helium, argon or Freon with pulsed pressure (U.S. Pat. No. 4,348,357); and hydrogen peroxide (U.S. Pat. Nos. 4,643,876 and 4,756,882). Sterilizing with ozone and singlet oxygen generated in a RF electric force field is described by U.S. Pat. No. 4,640,782. The plasma treatment found necessary to kill resistant spores has proven too severe for many packaging materials.

Typical prior art plasma sterilizing systems having a combination plasma generating and sterilizing chamber are exemplified by U.S. Pat. No. 4,643,876, for example. In these systems, the plasma is generated from hydrogen peroxide vapor and residue, and the article being sterilized is directly exposed to the plasma inducing electromagnetic field. The in situ generation of the ions and free radicals in the vicinity of the article surface is considered to be a critical part of the static process. Antimicrobial hydrogen peroxide pretreatment has been combined with exposure of the article to the electromagnetic plasma generating environment to remove any remaining hydrogen peroxide residues. The process is static, that is, the plasma is generated in the volume of gas initially in the closed chamber, and the articles are not exposed to plasma generated from a mixture of hydrogen, oxygen and inert gases, as in the process of this invention. These systems tend to rapidly decompose plastic and cellulose containing packages because o the strong oxidizing properties of the ions and free radicals in the elevated temperatures of the process. Limiting the process time to prevent package destruction also produces an incomplete spore kill rate.

Plasma gas sterilizer systems described in U.S. Pat. Nos. 3,851,436 and 3,948,601 comprise separate plasma RF generation chambers and sterilizing chambers. A gas plasma produced in the plasma generating chamber with argon, helium, nitrogen, oxygen or xenon is passed into a separate sterilization vacuum chamber containing the articles to be sterilized. These systems are not adequate for sterilizing contents of cellulose containing packages because the oxidizing plasma products degrade the packaging materials. They are not capable of producing a satisfactory spore kill rate without package damage.

Non-plasma gas sterilization procedures have been described using ozone (U.S. Pat. No. 3,704,096) and hydrogen peroxide (U.S. Pat. Nos. 4,169,123, 4,169,124, 4,230,663, 4,289,728, 4,366,125, 4,437,567 and 4,643,876). However, these procedures are not entirely effective or leave toxic residues on the articles being sterilized.

Peracid sterilization processes have been disclosed in East German Patent Application Serial No. 268,396, EPO Patent Application Publication No. 109,352 A1, and U.K. Patent 2,214,081, for example. The sporicidal activities of peracetic acid, alone and in combination with other compounds including ethanol and hydrogen peroxide are disclosed by Leaper, S., *Food Microbiology.* 1:199–203 (1984); Leaper, S. et al, *J.Applied Biol.* 64:183–186 (1988); Leaper, S., *J.Food Technology.* 19:355–360 (1984); and Leaper, S., *J.Food Technology* 19:695–702 (1984). These methods are not effective to sterilize the contents of packages containing cellulose and other materials which are reactive with peracid species.

The above apparatus and methods do not achieve 100 percent effective kill rates for many types of articles requiring sterilization, and most produce damage to articles and packaging in the course of producing high sporicidal kill rates. As a result, they do not achieve the necessary goal of providing an all purpose, one hundred percent effective sterilizing system and process.

SUMMARY AND OBJECTS OF THE INVENTION

The process of this invention for plasma sterilization comprises exposing an article in a sterilizing chamber to at least one cycle comprising a pulsed treatment with gaseous antimicrobial agent and a plasma treatment. The pulsed treatment comprises at least two pulse-vacuum cycles, each pulse-vacuum cycle comprising the steps of exposing the article to the gaseous antimicrobial agent at a pressure of from 4 to 8 torr and reducing the pressure in the sterilizing chamber to from 0.1 to 10 torr. The plasma treatment comprising exposing the article to a plasma generated from gases selected from the group consisting essentially of argon, helium, nitrogen, oxygen, hydrogen and mixtures thereof, the exposure to the plasma being carried out at a pressure of from 0.1 to 10 torr and a temperature of less than 80° C.

The antimicrobial agent is preferably selected from the group consisting of hydrogen peroxide, a peracid antimicrobial agent, and mixtures thereof, the peracid antimicrobial agent being selected from the group consisting of saturated and unsaturated peralkanoic acids having from 1 to 8 carbon atoms and halogenated derivatives thereof.

Optimally, the plasma is produced in a plasma generator and is fed therefrom to a sterilizing chamber. The article to be sterilized is located in the sterilizing chamber, and the antimicrobial agent vapor is introduced into the sterilizing chamber to expose the article located therein to said pretreatment. After said pretreatment, the pressure in the sterilizing chamber is reduced to a pressure not exceeding 10 torr, and the plasma is thereafter introduced into the sterilizing chamber.

Preferably, the plasma is generated from a gas mixture consisting essentially of argon, helium, nitrogen or mixtures thereof; from 1 to 21 (v/v) % oxygen; and from 1 to 20 (v/v) % hydrogen and optimally a gas mixture containing from 1 to 10% (v/v) oxygen and from 3 to 7% (v/v) hydrogen.

This pulsed treatment process is particularly suitable for sterilizing a porous article or an article enclosed in a porous container, the container being surrounded by the gas plasma during the treatment, even when the porous container comprises a carbohydrate composition.

One object of this invention is to provide a process which achieves one hundred percent spore skill rates with all types of articles used in the health care environment, including metallic articles and articles contained in porous sterile packages including cellulosic materials.

It is another object of this invention to provide a low pressure, low temperature plasma sterilization process which is one hundred percent effective for sterilizing packaged articles without destroying the integrity of the packages.

BRIEF DESCRIPTION OF THE DRAWINGS

FIG. 4 is a cross-sectional view of the plasma sterilizer embodiment of FIG. 3, taken along the line 4—4.

FIG. 5 is a cross-sectional view of tube 54 taken along line 5—5 in FIG. 3.

FIG. 6 is a cross-sectional view of tube 58 taken along line 6—6 in FIG. 3.

FIG. 7 is a cross-sectional view of tube 56 taken along line 7—7 in FIG. 3.

DETAILED DESCRIPTION OF THE INVENTION

Figure 1:
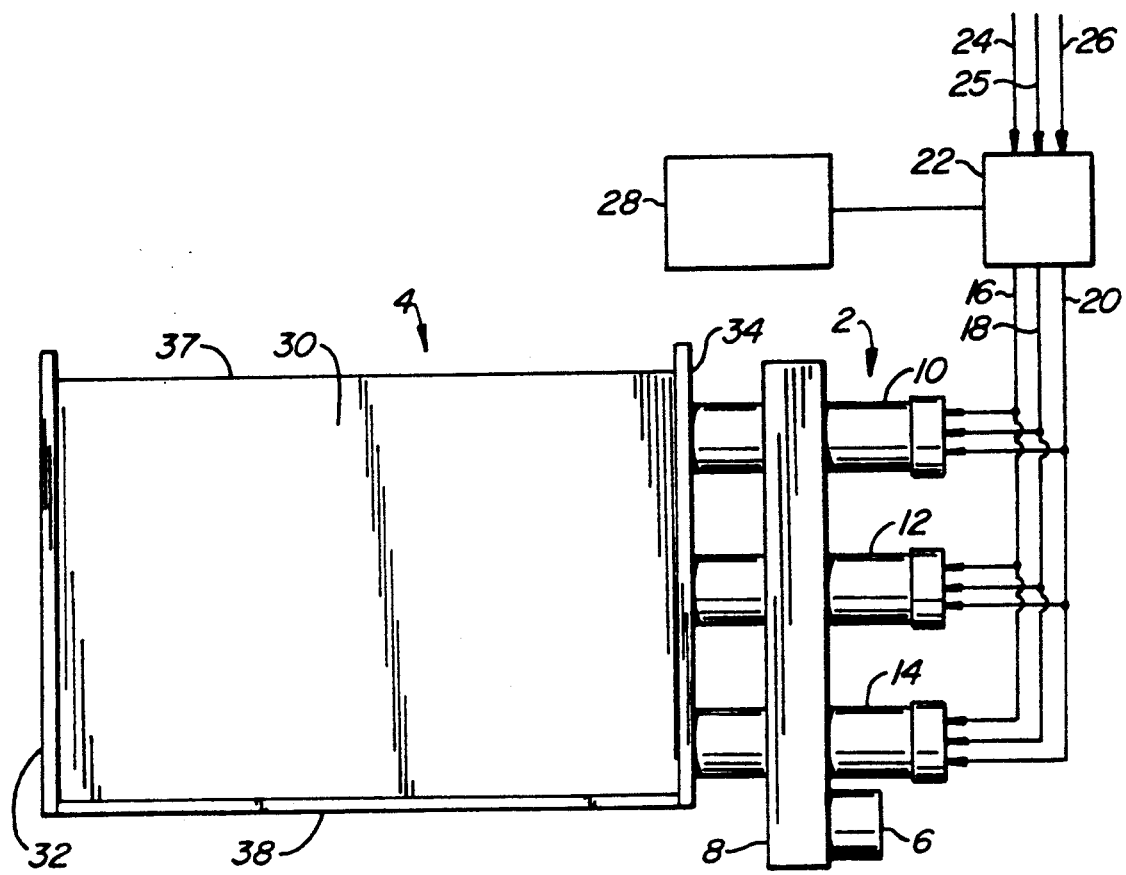
FIG. 1 is a top view of a plasma sterilizer of this invention.

Hospitals originally relied on disinfectants and steam autoclaves for sterilizing implements. In more recent years, ethylene oxide gas sterilization has made possible the sterilization of packaged articles, drugs and medical supplies, and hospital systems are highly dependent upon these procedures. Ethylene oxide is now known to be a dangerous carcinogen, however, and a number of new state laws protecting worker safety and the environment are precluding further use of ethylene oxide sterilizers in hospital environments.

Numerous gas plasma sterilizers using a wide variety of gases have been described in the literature. A few have been commercially produced. One system described in U.S. Pat. No. 4,643,876, for example, pretreats the article to be sterilized with hydrogen peroxide before it is placed in the electromagnetic field producing the plasma. It relies on the presence of the hydrogen peroxide residue in the electromagnetic field as a source of the plasma products and the direct exposure the hydrogen peroxide residue to the electromagnetic field to eliminate hydrogen peroxide residues. This system is suitable only for sterilizing non-metallic articles because of the focused heating of metallic articles and the destabilizing effect of metallic articles in plasma generating electromagnetic fields. This patent system is primarily designed for sterilizing non-metallic packaged goods. However, even with hydrogen peroxide pretreatment, one hundred percent spore kill rates are not achieved without severe degradation of the packaging materials.

Peracids such as peracetic acid are well known as sterilizing agents in situations where their residues can be tolerated or easily removed and where adequate exposure time is allowed. However, they are less active than hydrogen peroxide. They are also known to be ineffective for sterilizing goods packaged in the conventional cellulosic sterile packages used in the health care field.

This invention is based on the discovery that pulsed antimicrobial agent pretreatment of both packaged and unpackaged articles, followed by exposure of the articles to sterilizing gas plasmas, reliably and more efficiently kills one hundred percent of resistant spores at conditions which are not destructive to packaging materials. The exposure to the gas plasma in a sterilizing chamber separate from the plasma generating system protects the packaging and plastic components and permits the sterilization of metallic articles.

The term "sterilization" connotes a process by which all viable forms of microorganisms are destroyed or removed from an object. Since microorganisms die according to first order chemical kinetics, it is customary to define sterility in terms of "probability of survivors". The practical goal of a sterilization process is therefore measured as a probability (e.g., $10^{-3}$, $10^{-6}$, $10^{-12}$), the probability indicating the lethal effect of a particular sterilizing dose or regimen. It is usual to assume increased time of exposure to a set of sterilizing conditions will decrease the probability of survivors accordingly. Doubling the sterilizing time of identical conditions would result in a doubling of the exponent of the probability term, for example $10^{-6}$ would become $10^{-12}$.

The term "pretreatment" is used herein to define that at least one pulsed treatment of the article being sterilized with antimicrobial agent is followed by treatment with gaseous plasma products. The "pretreatment" with antimicrobial agent can follow one or more earlier plasma treatments and can be followed by one or more plasma treatments. Repetitions of the pulsed treatment and plasma gas treatment cycle any number of times can be used until total killing of spores with even the most resistant articles is achieved. The combination of peroxide and/or peracid antimicrobial agent and plasma gas treatments is synergistic in achieving a spore kill rate which exceeds the killing rate which can be achieved by use of hydrogen peroxide or peracid alone, or plasma gases alone, while preserving the integrity of packaging materials. The residues are also entirely eliminated by the plasma gases and vacuum.

The pulsed treatment comprises at least two and preferably at least 4 pulse-vacuum cycles. Each pulse-vacuum cycle comprises exposing the article to be sterilized to a pulse of gaseous antimicrobial agent at a pressure of from 4 to 18 torr and preferably a pressure of from 12 to 18 torr, and to a vacuum of less than 4 torr and preferably less than 1 torr. Each pulse of gaseous antimicrobial agent comprises exposure of the article to be sterilized to the antimicrobial agent for from 2 to 60 minutes and preferably from 5 to 15 minutes. The step of reducing the pressure in the sterilizing chamber can precede or follow the exposure of the article to be sterilized to the antimicrobial agent. The particular pulse-vacuum sequence order can be reversed as desired during successive repetitions of the pulsed treatment and plasma treatment cycle.

The term "peracid" as used herein, is defined to include well known peracid antimicrobial agents such as saturated and unsaturated peralkanoic acids including peraralkanoic acids having from 1 to 8 carbon atoms and halogenated derivatives thereof. Examples of suitable peracids include known peracetic acid, halogenated peracetic acids, performic acid, perpropionic acid, halogenated perpropionic acids, perbutanoic acid and its halogen derivatives, perisovaleric acid and its halogen derivatives, percapronic acid and its halogen derivatives, percrotonic acid, monopersuccinic acid, monoperglutaric acid, and perbenzoic acid, for example. The halogenated peracids contain one or more chloro, bromo, iodo or fluoro groups. The preferred peracids are sufficiently volatile to form an effective sporicidal vapor concentration at temperatures of less than 80° C.

In the pulsed treatment using hydrogen peroxide, the article is contacted with hydrogen peroxide vapors containing from 1 to 10% (v/v) and preferably from 2 to 8% (v/v) hydrogen peroxide vapor. The optimal vapor pretreatment involves contacting the article to be sterilized with hydrogen peroxide vapor in the sterilizing chamber. A total pulsed contact time of from 5 to 15 minutes is usually sufficient to insure contact of the entire surface of a packaged article with the hydrogen peroxide vapor.

In the pulsed treatment with peracid, peracid treatment is effected by contact of the article with antimicrobial concentrations of the peracid vapor. Preferably, the pulsed peracid pretreatment is carried out by exposing the article to be sterilized to peracid vapor having a concentration of from 1 to 35% (v/v) peracid and preferably from 6 to 12% (v/v) peracid for a time sufficient to permit contact of the vapor with all surfaces of the article being sterilized, packaged or unpackaged. The total pulsed contact exposure time is preferably from 5 to 15 minutes with packaged articles The peracid exposure can be carried out at a temperature of from 20° to 80° C. and preferably from 40° to 60° C.

Some peracids in certain concentrations are explosive at elevated temperatures. For this reason, peracetic acid is usually transported and stored in aqueous solutions having less than 35 wt. % peracetic acid. The peracetic acid solution is easily vaporized, and effective treatment of articles, according to this invention, can be achieved by exposing the articles to peracetic acid vapors at pressures in the range of from 1 to 18 torr, the lower pressure limit being the lower range limit of the effective concentration of the peracetic acid.

In the preferred process of this invention, the pulsed antimicrobial agent pretreatment is carried out with vapor introduced into the sterilizing chamber, and the article is pretreated with the peracid prior to exposing the article to the plasma. Suitable plasma sterilizing systems for carrying out the process of this invention are described in copending, commonly assigned U.S. patent application Ser. No. 07/475,602 filed Feb. 6, 1990, the entire contents of which are hereby incorporated by reference.

The process of this invention uses a plasma made from gas mixtures containing argon, helium and/or nitrogen; and oxygen and/or hydrogen, optionally containing inert gases and carbon dioxide. Nitrogen is not preferred because it can form toxic residues. The exhaust gas products fully satisfy current environmental and worker safety concerns, the products of the plasma being almost entirely water vapor, carbon dioxide and non-toxic gases normally found in the atmosphere.

The term "plasma" as used herein is defined to include any portion of the gas or vapors which contain electrons, ions, free radicals, dissociated and/or excited atoms or molecules produced as a result of the applied electric or electromagnetic field including any accompanying radiation which might be produced. The electromagnetic field can cover a broad frequency range, and can be produced by a magnetron, klystron or RF coil. For purposes of clarity of presentation and not by way of limitation, the description hereinafter describes the use of a magnetron as the electromagnetic field source, and the use of all other suitable sources of the electromagnetic field required for plasma production are intended to be included in this invention, including without limitation, magnetrons, klystron tubes, RF coils and the like.

Figure 2:
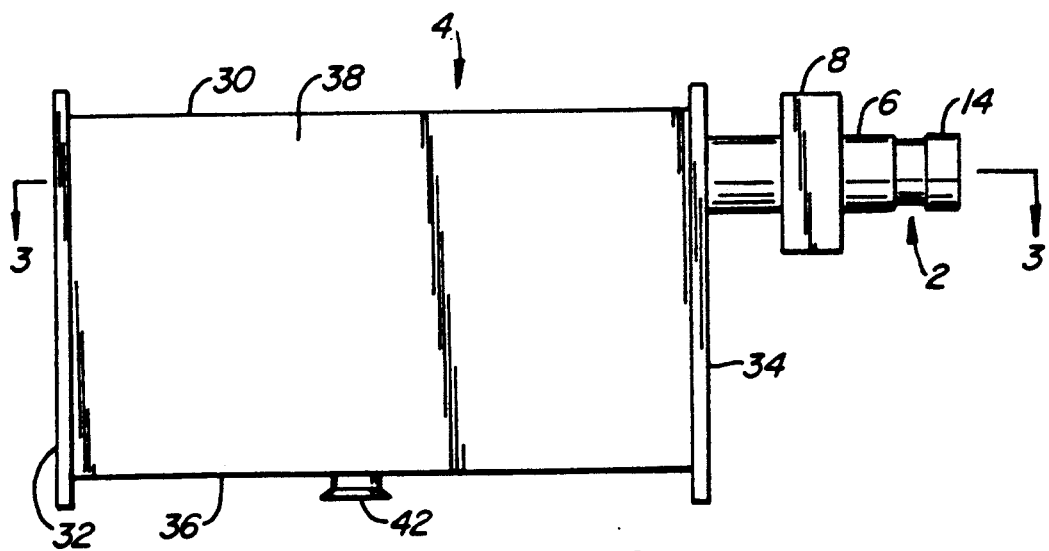
FIG. 2 is a front view of the plasma sterilizer embodiment of FIG. 1.

One suitable apparatus is shown in FIG. 1. FIG. 1 is a top view and FIG. 2 is a front view of a single waveguide plasma sterilizer embodiment of this invention.

The plasma sterilizer has a plasma generator 2 and a sterilizing chamber 4. The plasma generator 2 comprises an electromagnetic field generator such as a magnetron 6 and a waveguide 8 which directs the electromagnetic field. The plasma source gases are directed into plasma generating and delivering tubes 10, 12, and 14 by feeder tubes from gas delivery tubes 16, 18 and 20 leading from the control valve complex 22. Individual gases are fed from the pressured gas sources (not shown) by inlet lines 24, 25 and 26. The operation of the control valves in valve complex 22 is controlled by the central processing unit (CPU) 28 by standard procedures. The control valves and CPU can be any of the conventional, standard devices used for gas flow control in plasma generating equipment.

The sterilizing chamber 4 comprises top plate 30, side plates 32 and 34, bottom plate 36, back plate 37 and front sealing door 38 through which articles or materials to be sterilized are placed in the chamber. The plates are attached together in a sealed relationship to form a vacuum chamber, such as by welding. The door 38 is secured in a sealed relationship with the sterilizing chamber. It is hinged at the top, side or bottom with conventional hinge pins (structure not shown) to swing against abutting surfaces and an O-ring seal 40 (FIG. 3) of the side, top and bottom plates, where the pressure difference between the internal chamber vacuum pressure and the surrounding atmospheric pressure holds it tightly in place.

The plates and door can be made of any material having the strength required to withstand the external atmospheric pressure when the chamber is evacuated. Stainless steel or aluminum plates and door are preferred. The internal surface material of the chamber is critical and greatly affects the number of killing species available in the chamber. An optimum material is pure (98%) aluminum which can be applied either as a liner or as a flame-sprayed coating on all internal walls of the stainless steel chamber. An alternate material is nickel.

Antimicrobial additives are added as a liquid or vapor through conduit 35 to inlet port 39 (FIG. 4). The gases are exhausted from the sterilizing chamber through exhaust outlet port 42, isolation valve 43, and exhaust conduit 45 to a conventional vacuum pump system (not shown).

Figure 3:
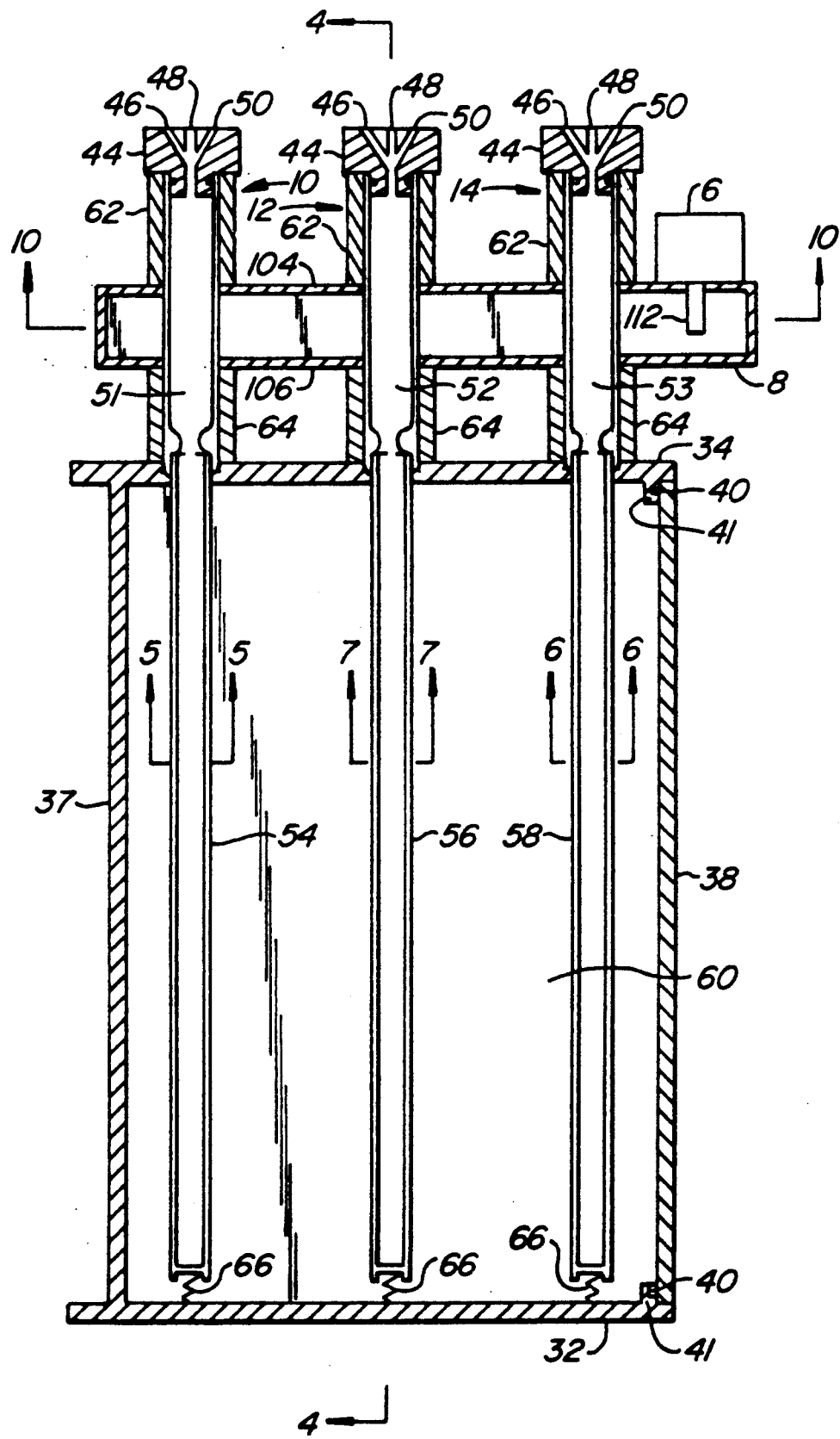
FIG. 3 is a cross-sectional view of the plasma sterilizer embodiment of FIG. 1 and FIG. 2, taken along the line 3—3 in FIG. 2.

FIG. 3 is a top cross-sectional view of the plasma sterilizer embodiment of FIG. 1 and FIG. 2, taken along the line 3—3 in FIG. 2. FIG. 4 is a side cross-sectional view of the plasma sterilizer embodiment of FIG. 1 and FIG. 3, taken along the line 4—4 in FIG. 3. Each of the plasma generators 10, 12 and 14 comprise an inlet cap 44 with gas inlet ports 46, 48 and 50 leading to a respective gas generator tube 51, 52 or 53 leading through the waveguide 8. In the waveguide 8, the gases are energized and convert in tubes 51, 52 and 53 to a plasma. The gas generator tube directs the plasma flow into the gas distribution tubes 54, 56 and 58 from which the plasma is fed into the sterilizing chamber 60. The gas generator tubes are enclosed in tubular metal cooling tubes 62 and 64. The caps 44 and the cooling tubes 62 and 64 are preferably provided with grooves or cooling fins (not shown) in a conventional manner to increase their efficiency in removing heat from gas generator tubes. The distal ends of the gas distribution tubes 54, 56 and 58 are supported by spring-biased end supports 66 mounted on sideplate 32.

The door 38 is held in sealing engagement by atmospheric pressure against the O-ring seal 40 mounted in the flange 41 extending from the side plates 32 and 34, and the top and bottom plates 30 and 36 (not shown). Optionally, additional conventional closure clamps or latches can be used to insure closure of the door before chamber evacuation is initiated.

FIG. 5, FIG. 6 and FIG. 7 are cross-sectional views of gas distribution tubes 54, 58 and 56, respectively, showing angular positions of the gas distribution outlet ports. The outlet ports are positioned to provide plasma flow to all lower portions of the sterilizing chamber 60 where articles to be sterilized are placed. Tube 54 shown in FIG. 5 is placed adjacent back plate 37 and directs plasma gases downward and toward the lower center of the chamber through outlet ports 70 and 72, respectively. Tube 58 shown in FIG. 6 is placed adjacent the door 38 and directs plasma gases downward and toward the lower center of the chamber through outlet ports 74 and 76, respectively. Tube 56 shown in FIG. 7 is placed in the central portion of the chamber 60 and directs plasma gases laterally downward through outlet ports 78 and 80. The outlet ports shown for the distribution tubes are representative and can be changed to any other configuration which achieves optimal plasma distribution to the sterilizing zone or zones of the chamber. Although only one angular arrangement is shown, each tube can have more than one angular set of outlet ports, each having different angles, along the length of the tube, as desired. The choice of outlet port angles and locations should be selected in view of how the articles to be sterilized are to be placed in the chamber and the type of article to be sterilized.

The plasma is directed through a change of direction, preferably at least 90°, before discharging it into the sterilizing chamber. This prevents direct impingement of hot plasma onto the articles being sterilized, greatly reducing the oxidation of sensitive packaging materials by the activated oxygen atoms in the plasma.

The apparatus can be used to generate a sterilizing plasma from a mixture of oxygen; argon, helium, and/or nitrogen; and hydrogen, or with a mixture of air and hydrogen, supplemented by oxygen or nitrogen to give the desired ratios. The sterilization is carried out at a vacuum pressure of from 0.1 to 10 torr and preferably from 1 to 3 torr. The temperature in the sterilizing chamber is maintained below 80° C. and preferably from 38° to 60° C. Under these conditions, effective sterilization is effected without significant deterioration of packaging materials in which articles to be sterilized may be placed.

Following pulsed treatment with antimicrobial agent, the sterilizing chamber is evacuated to a pressure of less than 10 torr. The article is then exposed to a plasma generated from a gaseous mixture of argon, helium or nitrogen mixed with oxygen and/or hydrogen at temperatures of less than 80° C., a pressure of from 0.1 to 10 torr, and a treatment time of at least 5, and preferably from 10 to 15 minutes. For sterilizing packaged goods, the gas mixtures from which the plasma is generated can contain from 1 to 21 (v/v) % oxygen and from 1 to 20 (v/v) % hydrogen, the balance being argon, helium and/or nitrogen and optional small quantities of inert gases.

The gas mixtures producing plasmas for sterilizing packages preferably contain from 1 to 10% (v/v) oxygen and from 2 to 8% (v/v) hydrogen, and optimally contain from 2 to 8% (v/v) oxygen and from 3 to 7% (v/v) hydrogen. Packages are treated for at least 15 minutes and preferably from 1 to 5 hours.

A preferred embodiment of the process of this invention comprising the following steps, after placing the articles to be sterilized in the sterilizing chamber:

1. The sterilizing chamber is evacuated to a pressure of 0.1 torr, and an isolation valve between the vacuum pump and sterilizing chamber is closed.
2. A pulse of peracetic acid, 2 ml, in the form of a 10 wt. % solution is admitted into the chamber to form a vapor, or sufficient peracetic acid vapor is introduced to produce a vapor, having a concentration of 2 mg/L peracetic acid.

Alternatively, a pulse of hydrogen peroxide, 2 ml, in the form of a 10 wt. % solution is introduced into the chamber to form a vapor, or sufficient hydrogen peroxide vapor is introduced to produce a vapor having a concentration of 2 mg/L hydrogen peroxide. If peracetic acid pretreatment is to be combined with hydrogen peroxide pretreatment, peracetic acid, 2 ml, in the form of a 10 wt. % solution is admitted into the chamber to form a vapor, or sufficient peracetic acid vapor is introduced to produce a vapor, having a concentration of 2 mg/L peracetic acid.

The pulse of peracetic acid and/or hydrogen peroxide vapor exposure is continued for from 5 to 15 minutes.
3. The pressure in the sterilizing chamber is reduced to less than 2 torr for from 1 to 2 minutes.
4. Steps 2 and 3 are repeated 4 times, and the chamber is evacuated to 0.1 torr.
5. Process gases are admitted to the plasma chamber, preferably at a flow rate of up to 5 liters per minute, and optimally from 3 to 4 liters per minute.
6. The magnetron is energized to create the plasma, and the plasma products flow into the sterilizing chamber.
7. The plasma treatment is continued for from 5 to 30 minutes and preferably from 5 to 15 minutes.
8. The magnetron is deactivated and the process gas flow to the plasma chamber is terminated.
9. Steps 1-8 are repeated until sterilization is complete and all spores are killed. Hydrogen peroxide and peracetic acid treatments can be alternated so that the pretreatment is limited to either one for a particular cycle repetition.
10. The isolation valve between the pump and chamber is closed, and the chamber is vented to the atmosphere. The sterilizing chamber can be pumped down and partially vented to remove acidic vapors before being fully vented to the atmosphere.

The above method sterilizes effectively in less time than is required without the pulsed antimicrobial agent treatment, particularly for porous articles and articles enclosed in porous packages. Furthermore, it is effective for sterilizing all materials, while plasma and peracids, alone, have limited ability.

We claim:

1. A process for plasma sterilization including exposing an article in a sterilizing chamber to at least one combination sterilizing cycle, each combination sterilizing cycle comprising:

a pulsed treatment with gaseous antimicrobial agent in the sterilization chamber, said pulsed treatment including one or more pulse-vacuum cycles, each pulse-vacuum cycle comprising the steps of exposing the article to the gaseous antimicrobial agent at a pressure of from 4 to 18 torr for a predetermined duration and removing the antimicrobial agent by evacuating the sterilizing chamber to a pressure of from 0.1 to 4 torr; and a plasma treatment comprising exposing the article in the sterilization chamber to a stream of plasma generated from gases consisting essentially of argon, helium, nitrogen, oxygen, hydrogen and mixture thereof, said plasma being generated in a separate plasma generating chamber and being supplied to the sterilizing chamber, the exposure of the article to the stream of plasma in the sterilizing chamber being carried out at a pressure of from 0.1 to 10 torr at a temperature of less than 80° C.

2. The process of claim 1, wherein the combination sterilizing cycle further includes an initial step of evacuating the sterilizing chamber prior to the one or more pulse-vacuum cycles.
3. The process of claim 1 wherein the pulsed treatment comprises at least 2 pulse-vacuum cycles.
4. The process of claim 1 wherein the pulsed treatment and plasma treatment cycle is repeated at least 2 times.
5. The process of claim 1 wherein the pulsed treatment cycle is preceded by a plasma treatment.
6. The process of claim 1 wherein the plasma is generated from a gas mixture consisting essentially of argon, helium, nitrogen oxygen and hydrogen or mixtures thereof; from 1 to 21 (v/v) % oxygen; and from 1 to 20 (v/v) % hydrogen and optimally a gas mixture containing from 1 to 10% (v/v) oxygen and from 3 to 7% (v/v) hydrogen.
7. The process of claim 1, wherein the pulsed treatment and the plasma treatment in each combination sterilizing cycle follow a predetermined order.
8. The process of claim 1 wherein the antimicrobial agent is selected from the group consisting of hydrogen peroxide, a peracid antimicrobial agent, and mixtures thereof, the peracid antimicrobial agent being selected from the group consisting of saturated and unsaturated peralkanoic acids having from 1 to 8 carbon atoms and halogenated derivatives thereof.
9. The process of claim 8 wherein the peracid antimicrobial agent is peracetic acid.
10. The process of claim 8 wherein the antimicrobial agent is halogenated peracetic acid.
11. The process of claim 8 wherein the antimicrobial agent is hydrogen peroxide.
12. The process of claim 8 wherein the antimicrobial agent is a mixture of peracetic acid and hydrogen peroxide.

* * * * *